United States Patent
Murphy et al.

(10) Patent No.: US 10,172,732 B2
(45) Date of Patent: Jan. 8, 2019

(54) UNIT AND DEVICE HAVING A UNIT FOR POSITIONING A PROSTHETIC COMPONENT

(71) Applicant: BIOTRONIK AG, Buelach (CH)

(72) Inventors: Brian Murphy, Galway (IE); Markus Hepke, Zurich (CH)

(73) Assignee: Biotronik AG, Buelach (CH)

( * ) Notice: Subject to any disclaimer, the term of this patent is extended or adjusted under 35 U.S.C. 154(b) by 580 days.

(21) Appl. No.: 14/397,638

(22) PCT Filed: May 2, 2013

(86) PCT No.: PCT/EP2013/059122
§ 371 (c)(1),
(2) Date: Oct. 28, 2014

(87) PCT Pub. No.: WO2013/167458
PCT Pub. Date: Nov. 14, 2013

(65) Prior Publication Data
US 2015/0119969 A1    Apr. 30, 2015

Related U.S. Application Data

(60) Provisional application No. 61/645,100, filed on May 10, 2012.

(51) Int. Cl.
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC .... A61F 2/95; A61F 2/962; A61F 2002/9517; A61F 2/966; A61F 2/954; A61F 2/2427; A61F 2/2436; A61B 17/12118
See application file for complete search history.

(56) References Cited

U.S. PATENT DOCUMENTS

| | | | | |
|---|---|---|---|---|
| 4,723,938 | A | * | 2/1988 | Goodin ............. A61M 25/1018 604/108 |
| 5,776,142 | A | * | 7/1998 | Gunderson ............... A61F 2/88 606/108 |

(Continued)

FOREIGN PATENT DOCUMENTS

| WO | 2005107644 A1 | 11/2005 |
|---|---|---|
| WO | 2011049808 A1 | 4/2011 |

OTHER PUBLICATIONS https://www.thefreedictionary.com/bushing, definition of the term "bushing," retrieved Oct. 21, 2017.*

*Primary Examiner* — David C Eastwood
(74) *Attorney, Agent, or Firm* — Wagenknecht IP Law Group PC

(57) ABSTRACT

A prosthesis delivery handle with a bushing (66) with two adjacent internal threads (64, 74) with different diameters and pitch surrounding a tubular threaded first shaft member (36) cooperating with the first thread (64) and a second inner member with a protrusion (82) extending through an axial slot in the tubular first member such that the protrusion runs in the second thread (74). First and second members are connected to an external shaft (112) and an internal element (102) so that when the bushing is rotated first and second members travel axially with different speeds the internal shaft and an external shaft move accordingly.

9 Claims, 3 Drawing Sheets

(56) References Cited

U.S. PATENT DOCUMENTS

| | | | | |
|---|---|---|---|---|
| 5,860,955 A * | 1/1999 | Wright | A61M 25/1018 604/98.01 |
| 6,110,151 A * | 8/2000 | Spool | A61M 25/1018 604/181 |
| 7,837,724 B2 * | 11/2010 | Keeble | A61F 2/95 623/1.11 |
| 2003/0191516 A1 * | 10/2003 | Weldon | A61F 2/95 623/1.12 |
| 2003/0199966 A1 * | 10/2003 | Shiu | A61F 2/95 623/1.12 |
| 2004/0127912 A1 * | 7/2004 | Rabkin | A61F 2/95 606/108 |
| 2005/0049667 A1 * | 3/2005 | Arbefeuille | A61F 2/07 623/1.11 |
| 2005/0149160 A1 * | 7/2005 | McFerran | A61F 2/95 623/1.11 |
| 2005/0182486 A1 * | 8/2005 | Gabbay | A61F 2/2409 623/2.11 |
| 2006/0184226 A1 * | 8/2006 | Austin | A61F 2/95 623/1.11 |
| 2007/0255390 A1 * | 11/2007 | Ducke | A61F 2/95 623/1.11 |
| 2008/0228258 A1 * | 9/2008 | Gerdts | A61F 2/95 623/1.11 |
| 2008/0294230 A1 * | 11/2008 | Parker | A61F 2/95 623/1.11 |
| 2009/0254165 A1 * | 10/2009 | Tabor | A61F 2/2412 623/1.11 |
| 2010/0094393 A1 * | 4/2010 | Cordeiro | A61F 2/95 623/1.11 |
| 2011/0257718 A1 * | 10/2011 | Argentine | A61F 2/966 623/1.11 |
| 2011/0257719 A1 * | 10/2011 | Argentine | A61F 2/95 623/1.11 |
| 2011/0270371 A1 * | 11/2011 | Argentine | A61F 2/95 623/1.11 |
| 2011/0270372 A1 * | 11/2011 | Argentine | A61F 2/95 623/1.11 |
| 2012/0046740 A1 | 2/2012 | Paul et al. | |
| 2013/0030519 A1 * | 1/2013 | Tran | A61F 2/2433 623/2.11 |
| 2014/0074226 A1 * | 3/2014 | Bielefeld | B25B 23/0064 623/2.11 |
| 2014/0228800 A1 * | 8/2014 | Rezac | A61M 25/0136 604/500 |
| 2014/0330219 A1 * | 11/2014 | Quint | A61F 2/95 604/264 |
| 2015/0119969 A1 * | 4/2015 | Murphy | A61F 2/966 623/1.11 |

* cited by examiner

Fig. 1
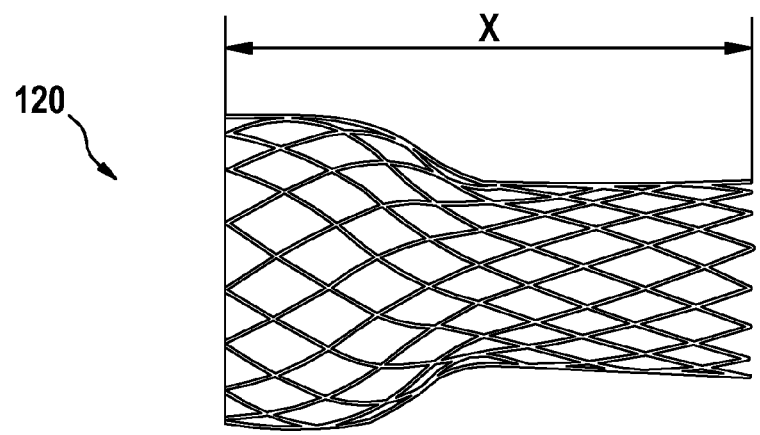
Fig. 1a
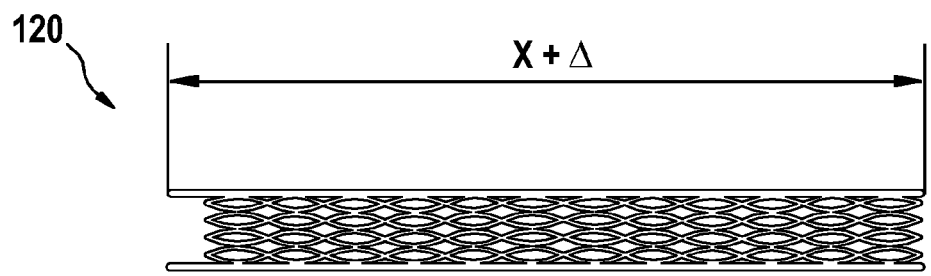
Fig. 1b

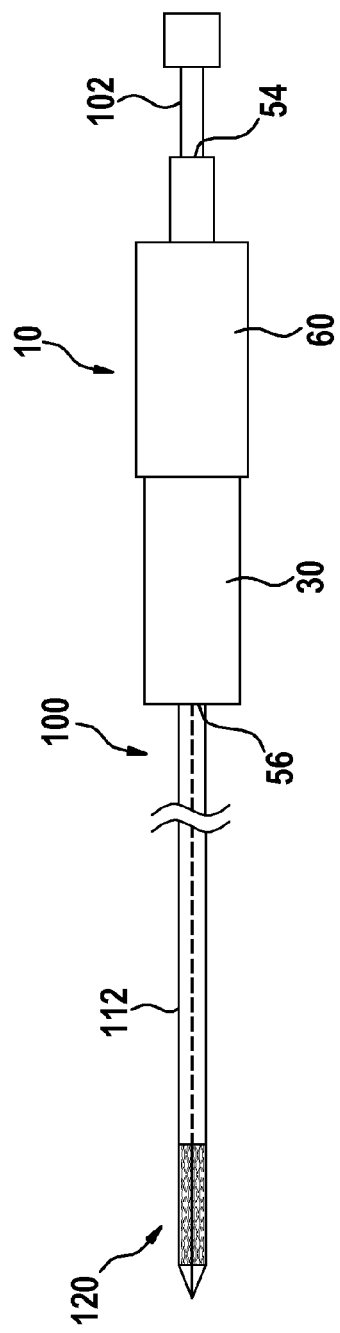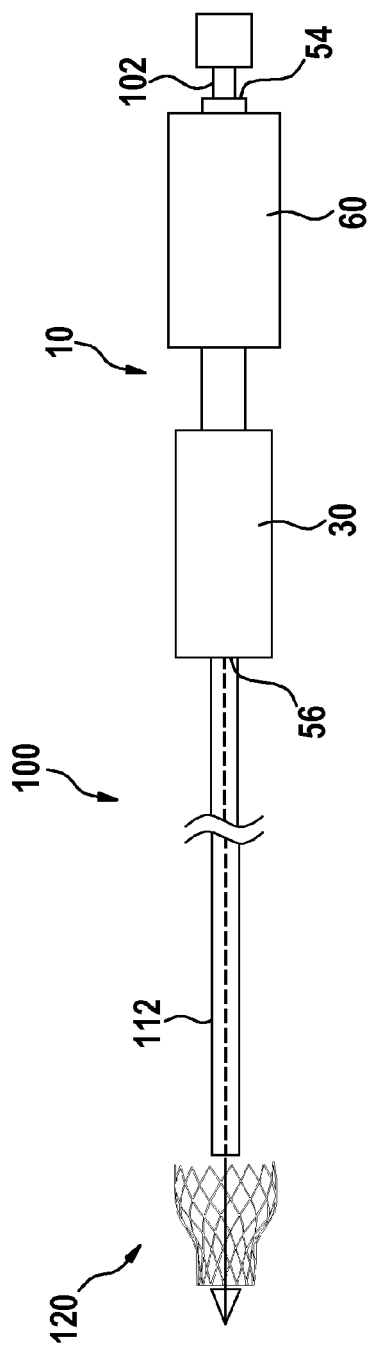

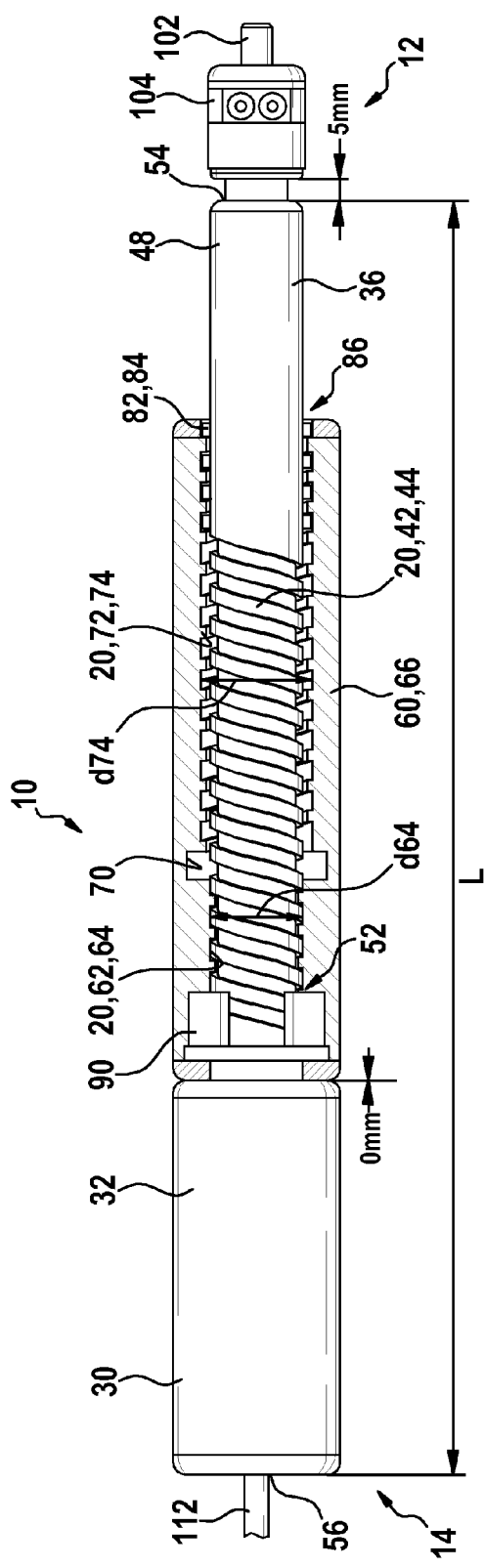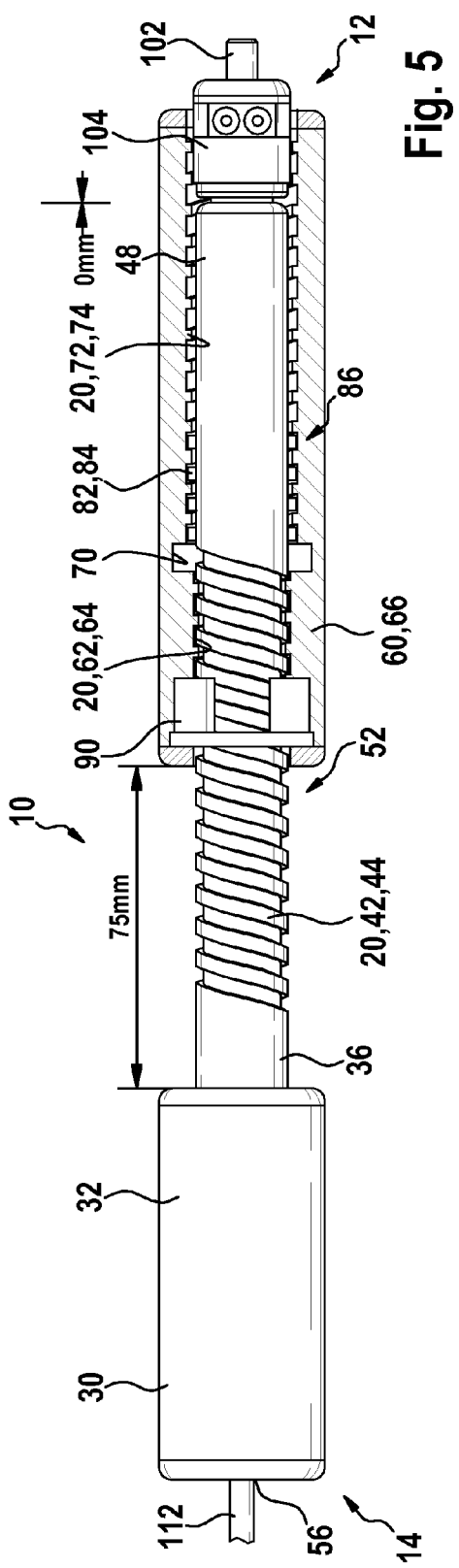

UNIT AND DEVICE HAVING A UNIT FOR POSITIONING A PROSTHETIC COMPONENT

TECHNICAL FIELD

The invention relates to a unit having at least a carrier part and a cooperating part for cooperating with the carrier part and a device having a unit for positioning a prosthetic component which allows a more accurate placement of the prosthetic device.

BACKGROUND OF THE INVENTION

It known in the art that a prosthetic component such as a stent or a prosthetic heart valve or the like is compressed to a small diameter for introducing the prosthetic component into a human or animal body. The prosthetic component is crimped onto a flexible internal shaft and covered by an external shaft. After introduction into the body, the external shaft is pulled back to release the prosthetic component at its desired place of delivery and the prosthetic device is expanded for positioning at the desired place of delivery. The length of the prosthetic component in the compressed state differs from the length of the prosthetic component in the expanded state. The length difference complicates a precise positioning of the prosthetic component at its place of delivery. As a result, the prosthetic component may have to be repositioned inside the human or animal body.

SUMMARY OF THE INVENTION

It is an object of the invention to provide a unit for improving the positioning of a component which has a length difference between a compressed and an expanded state.

Another object is to provide a device having such a unit for positioning a prosthetic component.

The objects are achieved by the features of the independent claims. The other claims, the description and the drawings provide advantageous developments of the invention.

In a first aspect of the invention a unit is proposed, the unit comprising at least a carrier part and a cooperating part for cooperating with the carrier part, wherein the carrier part and/or the cooperating part are comprising a control means which is configured for moving a first one of at least two elements in a different speed and/or different direction compared to a direction in which a second one of the elements is moving when the control means is activated in a state in which the elements are operationally connected to the unit.

The basic idea of the present invention is the compensation of the length differences of the prosthetic component in the compressed and the expanded state by a difference in the movement of a first one of at least two elements to a second one of the elements. The inventive difference in the movements of these elements could be achieved in various ways, either by different speeds and/or a different direction.

In an embodiment of the invention, both elements are moved in the same direction with different speed. The difference in the speed assures the compensation of the difference in the length of the prosthetic in the compressed and expanded state.

In the most preferred embodiment of the invention, the unit comprising at least a carrier part and a cooperating part for cooperating with the carrier part, wherein the carrier part and/or the cooperating part are comprising a control means which is configured for moving a first one of at least two elements in a direction opposite to a direction in which a second one of the elements is moving when the control means is activated in a state in which the elements are operationally connected to the unit.

The advantage is that a controlled movement of the elements in opposing directions facilitates a relative orientation and placement of one or both elements at a desired place of delivery. Particularly, the elements can be longitudinal elements such as an internal shaft for delivery of a prosthetic component and an external shaft for sheathing the internal shaft during introduction of the prosthetic component into a human or animal body.

Advantageously, the control means may be configured for moving the first one and the second one of the elements along different distances in a state in which the elements are operationally connected to the unit. The positioning of an element can be improved. Particularly, a length change of an element when positioned and/or released from the unit can be compensated.

According to another embodiment of the invention, the control means may comprise at least two control surfaces, wherein a first control surface is configured to move first guidable member and a second guiding surface is configured to move a second guidable member. At least two elements can be moved each in a controlled manner when the control means is activated. The control means can be arranged in one module so that a movement of the elements can be performed by a single module.

According to another embodiment of the invention, the first guidable member may be configured to cooperate with one of the elements and the guidable member may be configured to cooperate with another one of the elements in a state in which the elements are operationally connected to the unit. At least two elements can be moved each individually in a controlled manner when the control means is activated, each element having a specific control surface.

According to another embodiment of the invention, a bushing may comprise at least one of the control surfaces and a shaft may comprise at least another one of the control surfaces. Particularly, the bushing may be arranged coaxially with respect to the shaft thus providing a comfortable and compact design.

According to another embodiment of the invention, the bushing may have at least two internal threads arranged along a longitudinal extension of the bushing. Advantageously, one of the internal threads may have a smaller diameter than another one of the internal threads. One bushing can cooperate with two different guidable members such as an external thread and/or pins being guided by one of the bushing's threads. This arrangement facilitates the design of the unit, providing a compact unit which can be easily manufactured. The threads may both be left-handed threads or both right-handed threads.

According to another embodiment of the invention, one of the internal threads may have a smaller pitch than another one of the internal threads. This allows for a different travel distance of elements which are moved by ways of the threads. The movement can be performed with high accuracy by selecting an appropriate difference in the thread pitches.

According to another embodiment of the invention, the shaft may be configured to cooperate with an inner one of the elements. This allows for employing elements which are arranged coaxially with respect to each other.

Advantageously, the shaft may be configured for allowing cooperation of a guidable member with at least one of the internal threads of the bushing. This allows for employing elements which are arranged coaxially with respect to each other.

According to another embodiment of the invention, the shaft may have an external thread region which cooperates with a first one of the internal threads of the bushing, particularly with the internal thread having the smaller diameter. This arrangement allows for a compact design.

According to another embodiment of the invention, the shaft may have an opening for allowing cooperation of one of the internal threads of the bushing with a guidable member disposable on one of the elements surrounded by the shaft. This allows for a compact design when the elements are arranged coaxially.

According to another embodiment of the invention, the bushing may be configured to cooperate with an element at least partially surrounding the inner one of the elements. Advantageously, the shaft may provide an opening for the inner one of the elements protruding through the shaft in axial direction.

According to another embodiment of the invention, the unit may be configured as a twist-grip handle, thus providing a comfortable design which can be easily be activated by an operator.

According to another aspect of the invention, a device is provided for placing a prosthetic component, the device comprising a unit according to anyone of features described above, the unit comprising at least a carrier part and a cooperating part for cooperating with the carrier part, the carrier part and/or the cooperating part comprising at least one control means configured for moving a first one of at least two elements in a direction opposite to a direction in which a second one of the elements is moving when the control means is activated in a state in which the elements are operationally connected to the unit.

The unit allows for compensation of a length difference of the prosthetic component in a compressed and in an expanded state so that the positioning of the prosthetic component can be performed more accurately and safely. This reduced the necessity for repositioning the prosthetic component and facilitates the introduction of a prosthetic component into a human or animal body.

According to an embodiment of the invention, the at least two elements may comprise an internal shaft for carrying the prosthetic component and an external shaft for sheathing the prosthetic device at least temporarily. The unit can be coupled to a well-known design of a catheter, for instance.

According to another embodiment of the invention, the internal shaft may protrude through the unit at its proximal end, thus limiting the overall length of the device.

According to another embodiment of the invention, the internal shaft may be connected or connectable to a second guidable member which protrudes through an opening of the carrier part and cooperates with a control surface of the cooperating part. For instance, the internal shaft may carry pins which can engage a control surface of the cooperating part which surrounds the carrier part.

BRIEF DESCRIPTION OF THE DRAWINGS

The present invention together with the above-mentioned and other objects and advantages may best be understood from the following detailed description of the embodiments, but not restricted to the embodiments, wherein is shown in:

FIG. 1a, 1b in a side view a prosthetic device in an expanded (FIG. 1a) and in a compressed state (FIG. 1b);

FIG. 2 in a schematic side view an embodiment of a device according to the invention in a first operational state with a prosthetic component in a compressed state;

FIG. 3 in a schematic side view an embodiment of a device according to the invention in a second operational state with a prosthetic component in an expanded state;

FIG. 4 in a partially cut side view an embodiment of a unit according to the invention in a first operational state to FIG. 2; and FIG. 5 in a partially cut side view an embodiment of a unit according to the invention in a second operational state to FIG. 3.

DETAILED DESCRIPTION OF PREFERRED EMBODIMENTS

In the drawings, like elements are referred to with equal reference numerals. The drawings are merely schematic representations, not intended to portray specific parameters of the invention. Moreover, the drawings are intended to depict only typical embodiments of the invention and therefore should not be considered as limiting the scope of the invention.

FIGS. 1a and 1b illustrate by ways of example an example embodiment of a prosthetic component 120 in an expanded state (FIG. 1a), e.g. before being mounted to a catheter or after being released from the catheter, and in a compressed state (FIG. 1b), when being crimped on the internal shaft of the catheter (not shown). In the compressed state, the prosthetic component 120 has a length of $X+\Delta$, while its length in the expanded state the length is X. In a realistic example, the length difference of a stent between the two states may be several, for instance 5, millimeters.

FIGS. 2 and 3 depict in a schematic side view an example embodiment of a device 100 according to the invention in a first operational state (FIG. 2) and a second operational state (FIG. 3). The first operational state may correspond to a state before and during introduction of the device 100 into the human or animal body. The second operational state may correspond to a state where the prosthetic device 120 expands or is expanded.

The device 100 is provided for placing a prosthetic component 120 at a desired place of delivery in a human or animal body. Device 100 comprises a unit 10 as described in FIGS. 4 and 5 in more detail, and comprises an internal shaft (element 102) for carrying the prosthetic component 120 and an external shaft (element 112) for sheathing the prosthetic device 120 at least temporarily. Unit 10 is arranged at a proximal side of the device 100 and the prosthetic device 120 is arranged at a distal side of the device 100. The internal shaft (element 102) or an internal-shaft holder may protrude through an opening 54 from unit 10 to the proximal end of unit 10, while the external shaft (element 112) through which the internal shaft extends protrudes through an opening 56 at the distal end of unit 10.

Unit 10 is, for instance, formed as a twist-grip handle and comprises a carrier part 30 and a cooperating part 60. The cooperating part 60 can be rotated which moves the cooperating to the proximal end of device 100 (towards the right-hand side of the drawing). The cooperating part 60 is connected to the external shaft (element 112) which is accordingly pulled to the proximal side. While the external shaft (element 112) is pulled for a distance long enough to uncover the prosthetic device 120, the prosthetic device 120 expands and becomes shorter than in the compressed state.

While the external shaft (element 112) moves to the proximal end, the internal shaft (element 102) is pushed towards the opposite, distal direction for compensating the shortening of the prosthetic device 120 during expansion by way of action of unit 10 as described in the following Figures. The way of the internal shaft (element 102) may be much shorter than the way of the external shaft (element 112).

FIG. 4 depicts in a partially cut side view an embodiment of a unit 10 according to the invention in a first operational state, corresponding to an operational state depicted in FIG. 2, and FIG. 5 illustrates in a partially cut side view an embodiment of a unit according to the invention in a second operational state, corresponding to an operational state depicted in FIG. 3.

As can be seen in FIGS. 4 and 5, unit 10 may be coupled to a device for delivery a prosthetic component 120 (FIGS. 2, 3). However, the unit 10 can also be employed for other purposes. Compensating can be in corrected for in both the opposite direction (as shown in this embodiment of the invention) or the same direction (not shown) whichever is deemed most advantageous.

Unit 10 has a proximal end 12 and a distal end 14 and a longitudinal extension L. The first operational state may be a state in which the prosthetic component 120 (FIGS. 2, 3) is still arranged on an internal shaft (inner element 102) in a crimped state where the prosthetic component may be longer than in an expanded state. The second operational state may be a state in which the prosthetic component 120 (FIGS. 2, 3) is expanded or partially expanded where the prosthetic component 120 (FIGS. 2, 3) is shorter than in the crimped state. The unit 10 can advantageously compensate for this difference in length.

The unit 10 comprises at least a carrier part 30 and a cooperating part 60 for cooperating with the carrier part 30. The carrier part 30 and the cooperating part 60 of the unit 10 may be a configured as a twist-grip handle. Carrier part 30 may have a handle part 32 and a threaded shaft 36. Shaft 36 comprises, for instance, a region with an external thread 44 and an unthreaded region 48 at the proximal end 12.

Cooperating part 60 may be embodied as a bushing 66 which can be moved along the threaded shaft 36. Handle part 32 may have a larger diameter than thread 44 and thus provide an end stop for bushing 66 towards the distal end 14. When operating unit 10, an operator holds unit 10 at a handle part 32 of carrier part 30 and rotates the bushing 66 which moves along the threaded shaft 36 towards the proximal end 12.

Carrier part 30 and cooperating part 60 comprise control means 20 configured for moving the first element 102 of the at least two elements 102, 112 in a direction opposite to a direction in which the second element 112 of the elements 102, 112 is moving when the control means 20 is activated in a state in which the elements 102, 112 are operationally connected to the unit 10. For instance, internal shaft (element 102) is connected to an inner-shaft holder 104 which secures the internal shaft axially.

Control means 20 may advantageously also be configured for moving the first one of the elements 102 along a different, e.g. shorter, distance than the second one of the elements 112 in a state in which the elements 102, 112 are operationally connected to the unit 10. Control means 20 comprises at least two control surfaces 42, 72, wherein the first control surface 42 is configured to cooperate with a first guidable member 62 and a second control surface 72 is configured to cooperate with a second guidable member 82.

One of the control surfaces, e.g. control surface 42, is configured to cooperate at least indirectly with one of the elements 112 and another one (control surface 72) is configured to cooperate with element 102 at least indirectly in a state in which the elements 102, 112 are operationally connected to the unit 10.

Bushing 66 has internal threads 64, 74 arranged in series along the longitudinal extension L. the internal thread 74 may constitute the control surface 72. the internal threads 64, 74 have different diameters d64, d74 and different thread pitches which allows for each thread to cooperate with another guided element and which allows for each element to travel with a different speed (and, hence, distance) when the bushing 66 is turned about the shaft 36. for instance, diameter d64 is smaller than diameter d74.

Shaft 36 has an external thread 44 which constitutes a control surface 42. External thread 44 guides the internal thread 64 as guidable member 62. External thread 44 cooperates with internal thread 64 of bushing 66. Thread 64 moves outer-shaft holder 90 which is connected to the external shaft (element 112) by an axial opening 52 in the shaft 36.

When bushing 66 is rotated about shaft 36, the external shaft (element 112) is pulled to the right hand side in the drawing towards the proximal end 12 of unit 10.

Shaft 36 is configured for allowing cooperation of a guidable member 82 with the second internal thread 74 of the bushing 66. Shaft 36 has an opening 86 in axial direction so that guidable member 82 can protrude through shaft 36 in radial direction for allowing cooperation of internal thread 74 of bushing 66 with the guidable member 82. Guidable member 82 can be disposed on inner element 102 surrounded by the shaft 36.

Guidable member 82 may be embodied as pins 84 or a threaded segment which move along thread 74 when bushing 66 is rotated. The pins 84 are connected to the inner element 102 and protrude through the opening 86 of shaft 36.

Because diameter d74 is larger than diameter d64, the pins 84 can only move along thread 74, and thread 64 can only move along thread 44.

Hence, when rotating bushing 66, the pins 84 are forced along thread 74 to move towards the distal end 14, and hence the internal shaft (inner element 102) moves towards the distal end 14 of unit 10. Because of the different thread pitches of threads 64, 74 (control surfaces 62, 72), the internal shaft (element 102) travels a shorter distance towards the distal end 14 than the external shaft (element 112) travels towards the proximal end 12. This travel distance of the internal shaft compensates for the length difference of the prosthetic component 120 (FIGS. 2, 3) being released when the external shaft is pulled away from the internal shaft.

Shaft 36 provides an opening 54 for the internal shaft (inner element 102) so that the inner element 102 can protrude freely through the shaft 36 in axial direction.

When comparing FIGS. 4 and 5 it is clearly to be seen that, while bushing 66 is rotated about external thread 44 of shaft 36, thus pulling outer element 112 to the proximal end 12, the inner element 102 (internal shaft) is pushed to the distal end 14 for several millimeters. For instance, the outer element 112 is pulled by e.g. 75 mm towards the proximal end 12 while at the same time the inner element 102 is pushed to the distal end by e.g. 5 millimeters.

What is claimed is:

1. A device (100) for placing a prosthetic component (120), the device (100) comprising a unit (10) operationally connected to an inner element (102) and an outer element (112), between which is configured for placement of a prosthetic component (120), wherein the unit (10) comprises a carrier part (30) comprising a threaded shaft (36) and a cooperating part (60) comprising two sets of internal threads (64, 74) having a different diameter from one another and arranged in series along a longitudinal extent of the cooperating part (60), wherein one set of the internal threads (64) is guided by the threaded shaft (36) to move the outer element (112) and another set of the internal threads (74) cooperates with a guidable member (82) that extends radially through the threaded shaft (36) to move the inner element (102) in a direction opposite to the movement of the outer element (112), thereby sheathing or unsheathing the prosthetic component.

2. The device according to claim 1, wherein rotation of the cooperating part (60) moves the inner and outer elements (102, 112) along different distances.

3. The device according to claim 1, wherein one of the sets of internal threads (64) has a smaller pitch than the other set of the internal threads (74).

4. The device according to claim 1, wherein the threaded shaft (36) cooperates with the set of internal threads (64) having the smaller diameter.

5. The device according to claim 1, wherein the threaded shaft (36) has an opening (86) through which the guidable member (82) radially extends from the inner element (102).

6. The device according to claim 1, wherein the unit (10) is configured as a twist-grip handle.

7. The device according to claim 1, wherein the internal shaft (102) protrudes through the unit (10) at its proximal end (12).

8. The device according to claim 1, wherein the internal shaft is connected to the guidable member (82).

9. A device (100) for placing a prosthetic component (120), the device (100) comprising a unit (10) operationally connected to an inner element (102) and an outer element (112), between which is configured for placement of a prosthetic component (120), wherein the unit (10) comprises a carrier part (30) comprising a threaded shaft (36) and a cooperating part (60) comprising two sets of internal threads (64, 74) having a different diameter from one another and arranged in series along a longitudinal extent of the cooperating part (60), wherein one set of the internal threads (64) is guided by the threaded shaft (36) to move the outer element (112) and another set of the internal threads (74) cooperates with a guidable member (82) that extends radially through the threaded shaft (36) to move the inner element (102) along a different distance and/or a different speed than the outer element (112), thereby sheathing or unsheathing the prosthetic component.

\* \* \* \* \*